(12) United States Patent
Turos et al.

(10) Patent No.: US 8,143,398 B1
(45) Date of Patent: Mar. 27, 2012

(54) ACTIVITY OF NEW N-ACYLATED CIPROFLOXACIN DERIVATIVES AGAINST FACULATIVE INTRACELLULAR BACTERIA

(75) Inventors: Edward Turos, Wesley Chapel, FL (US); Burt E. Anderson, Valrico, FL (US); Ryan Scott Cormier, Tampa, FL (US); John C. Thomas, Lake City, FL (US); Rebecca J. Kapolka, Pinellas Park, FL (US); Glenn Roma, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/031,991

(22) Filed: Feb. 22, 2011

Related U.S. Application Data

(60) Provisional application No. 61/306,224, filed on Feb. 19, 2010.

(51) Int. Cl.
*C07D 241/04* (2006.01)

(52) U.S. Cl. ...................................... 544/357
(58) Field of Classification Search .................. 544/362
See application file for complete search history.

(56) References Cited

U.S. PATENT DOCUMENTS 4,559,341 A * 12/1985 Petersen et al. .......... 514/253.08

OTHER PUBLICATIONS

Ives, In vitro susceptibilities of *Bartonella* and *Rickettsia* spp. to fluoroquinolone antibiotics as determined by immunofluorescent antibody analysis of infected Vero cell monolayers, 2001, International Journal of Antimicrobial Agents, vol. 18, p. 217-222.*
Rolain et al., Recommendations for Treatment of Human Infections Caused by *Bartonella* Species, Antimicrobial Agents and Chemotherapy, 2004, vol. 48, No. 6, pp. 1921-1933.
Fung-Tomc et al., Antibacterial Spectrum of a Novel Des-Fluoro(6) Quinolone, BMS-284756, Antimicrobial Agents and Chemotherapy, 2000, vol. 44, No. 12, pp. 3351-3356.
Minnick et al., gyrA Mutations in Ciprofloxacin-Resistant *Bartonella bacilliformis* Strains Obtained In Vitro, Antimicrobial Agents and Chemotherapy, 2003, vol. 47, No. 1, pp. 383-386.
Drlica et al., DNA Gyrase, Topoisomerase IV, and the 4-Quinolones, Microbiology and Molecular Biology Reviews, 1997, vol. 61, No. 3, pp. 377-392.
Anderson et al., *Bartonella* spp. as Emerging Human Pathogens, Clinical Microbiology Reviews, 1997, vol. 10, No. 2, pp. 203-219.

* cited by examiner

*Primary Examiner* — Andrew D Kosar
*Assistant Examiner* — Karen Cheng
(74) *Attorney, Agent, or Firm* — Wanhua Zhao; Smith & Hopen, P.A.

(57) ABSTRACT

*Bartonella* species are facultative intracellular pathogens responsible for a range of diseases in animals and in humans. A selection of N-acyl ciprofloxacin analogues, chemically synthesized from ciprofloxacin, have been tested in vitro for activity against *Bartonella* species as models for therapeutic development. Nine *Bartonella* strains, including five of *B. henselae*, two of *B. quintana*, and one each of *B. elizabethae* and *B. vinsonii*, have been tested for susceptibility to different N-acyl ciprofloxacin derivatives. Several techniques have been used to test the in vitro antibacterial activity of the derivatives. Seven of them, labeled RC4-125, RC4-143, RC4-147, RC5-28, RC5-29, RC5-32 and RC5-69 showed significant intracellular anti-*Bartonella* activity. These synthetically derived N-acyl ciprofloxacin derivatives may be useful in the therapeutic treatment of infections caused by *Bartonella*.

2 Claims, 5 Drawing Sheets

| Strain | N- acyl ciprofloxacin derivatives | | | | | | | | | | | | | | | | Controls | | | |
|---|---|---|---|---|---|---|---|---|---|---|---|---|---|---|---|---|---|---|---|---|
| | 125 | | 129 | | 139 | | 141 | | 143 | | 145 | | 147 | | Rifampin | | DMSO | |
| | Zone | MIC | Zone | MIC | Zone | MIC | Zone | MIC | Zone | MIC | Zone | MIC | Zone | MIC | Zone | MIC | Zone | MIC |
| B. henselae Houston-1 "smooth" | 65 | 1.0-10 | 6 | 1.0-10 | 51 | 0.5-1.0 | 52 | 1.0-5.0 | 50 | 0.1-0.5 | 32 | 1.0-10 | 56 | 0.1-0.2 | 48 | 0.03-0.06* | 6 | >>>10 |
| B. henselae Houston-1 "rough" | 52 | 1.0-10 | 35 | 1.0-10 | 56 | 0.5-1.0 | 60 | 1.0-5.0 | 51 | 0.1-0.5 | 32 | 1.0-10 | 55 | 0.1-0.2 | 56 | 0.03-0.06* | 6 | >>>10 |
| B. henselae SD-2 | 57 | 1.0-10 | 29 | 1.0-10 | 56 | 0.5-1.0 | 50 | 1.0-5.0 | 58 | 0.1-0.5 | 29 | 1.0-10 | 56 | 0.1-0.2 | 49 | 0.03-0.06* | 6 | >>>10 |
| B. henselae SA-1 | 52 | 1.0-10 | 6 | 1.0-10 | 50 | 0.5-1.0 | 53 | 1.0-5.0 | 52 | 0.1-0.5 | 27 | 1.0-10 | 58 | 0.1-0.2 | 47 | 0.03-0.06* | 6 | >>>10 |
| B. elizabethae | 58 | 1.0-10 | 21 | 1.0-10 | 26 | 0.5-1.0 | 28 | 1.0-5.0 | 34 | 0.1-0.5 | 20 | 1.0-10 | 37 | 0.1-0.2 | 42 | 0.03* | 6 | >>>10 |
| B. henselae Marseille | 61 | 1.0-10 | 31 | 1.0-10 | 35 | 0.5-1.0 | 34 | 1.0-5.0 | 38 | 0.1-0.5 | 19 | 1.0-10 | 42 | 0.1-0.2 | 16 | 0.03-0.06* | 6 | >>>10 |
| B. quintana Fuller | 6 | 1.0-10 | 11 | 1.0-10 | 29 | 0.5-1.0 | 30 | 1.0-5.0 | 27 | 0.1-0.5 | 16 | 1.0-10 | 30 | 0.1-0.2 | 44 | 0.06-0.25* | 6 | >>>10 |
| B. quintana D-Perm | 47 | 1.0-10 | 6 | 1.0-10 | 29 | 0.5-1.0 | 28 | 1.0-5.0 | 27 | 0.1-0.5 | 16 | 1.0-10 | 32 | 0.1-0.2 | 40 | 0.06-0.25* | 6 | >>>10 |
| B. vinsonii | 6 | 1.0-10 | 20 | 1.0-10 | 39 | 0.5-1.0 | 29 | 1.0-5.0 | 38 | 0.1-0.5 | 18 | 1.0-10 | 45 | 0.1-0.2 | 39 | 0.12* | 6 | >>>10 |

Figure 5

| Strain | N-acyl ciprofloxacin Derivatives | | | | | | | | | | | | | | Controls | | | |
|---|---|---|---|---|---|---|---|---|---|---|---|---|---|---|---|---|---|---|
| | RC5-17 | | RC5-28 | | RC5-29 | | RC5-32 | | RC5-48 | | RC5-58 | | RC5-69 | | Rifampin | | DMSO | |
| | zone | m.c. | zone | m.c. | zone | m.c. | zone | m.c. | zone | m.c. | zone | m.c. | zone | m.c. | | m.c. | zone | m.c. |
| B. henselae Houston-1 "smooth" | 65 | 0.1 | 56 | 0.1 | 34 | 0.1 | 40 | 0.5 | 52 | 0.5 | 62 | 0.5 | 43 | 0.5 | 48 | 0.03-0.06* | 6 | >>>10 |
| B. henselae Houston-1 "rough" | 52 | 0.1 | 60 | 0.1 | 68 | 0.1 | 61 | 0.5 | 60 | 0.2 | 43 | 0.5 | 35 | 0.5 | 56 | 0.03-0.06* | 6 | >>>10 |
| B. henselae SD-2 | 57 | 0.1 | 66 | 0.1 | 52 | 0.1 | 41 | 0.5 | 50 | 0.5 | 54 | 0.5 | 40 | 0.5 | 49 | 0.03-0.06* | 6 | >>>10 |
| B. henselae SA-1 | 52 | 0.1 | 59 | 0.1 | 44 | 0.1 | 38 | 0.5 | 53 | 0.5 | 49 | 0.5 | 39 | 0.5 | 47 | 0.03-0.06* | 6 | >>>10 |
| B. elizabethae | 58 | 0.1 | 53 | 0.1 | 44 | 0.1 | 36 | 0.5 | 28 | 0.5 | 37 | 0.5 | 30 | 0.5 | 42 | 0.03* | 6 | >>>10 |
| B. henselae Marseille | 61 | 0.2 | 63 | 0.1 | 48 | 0.1 | 42 | 0.5 | 34 | 0.5 | 38 | 0.5 | 27 | 0.5 | 16 | 0.03-0.06* | 6 | >>>10 |
| B. quintana Fuller | 62 | 0.2 | 58 | 0.2 | 32 | 0.2 | 33 | 0.8 | 30 | 1.0 | 36 | 1.0 | 17 | 0.8 | 44 | 0.06-0.25* | 6 | >>>10 |
| B. quintana D-Perm | 47 | 0.1 | 54 | 0.2 | 42 | 0.2 | 38 | 0.8 | 28 | 1.0 | 32 | 1.0 | 16 | 0.8 | 40 | 0.06-0.25* | 6 | >>>10 |
| B. vinsonii | 68 | 0.1 | 69 | 0.1 | 50 | 0.1 | 36 | 0.5 | 29 | 1.0 | 40 | 0.5 | 29 | 0.5 | 39 | 0.12* | 6 | >>>10 |

Figure 6

ACTIVITY OF NEW N-ACYLATED CIPROFLOXACIN DERIVATIVES AGAINST FACULATIVE INTRACELLULAR BACTERIA

CROSS-REFERENCE TO RELATED APPLICATION

This application claims priority from U.S. Provisional Application No. 61/306,224 filed on Feb. 19, 2010, entitled "Bartonella as a Model Intracellular Pathogen for Developing Therapeutics".

STATEMENT OF GOVERNMENT INTEREST

This invention was made with government support under HR0011-08-0087 awarded by the Department of Defense/Defense Advanced Research Projects Agency. The government has certain rights in the invention.

FIELD OF INVENTION

This invention relates to the field of treating pathogens and infectious diseases.

BACKGROUND OF INVENTION

Bartonella is a genus of Gram-negative, facultative intracellular bacteria. Bartonella species are responsible for a range of diseases in animals and in humans. Some species have been recognized as emerging pathogens. The wide range of disease manifestations caused by Bartonella depends on the infecting species and the immune status of the patient. Most Bartonella species are sensitive to quinolones in vitro, though treatment failures have been reported. Quinolones vary in their antibacterial spectrum and activity. Fluoroquinolones, a type of quinolone, effectively inhibit DNA synthesis by disrupting DNA breakage-reunion reactions. Ciprofloxacin is a fluoroquinolone that inhibits the bacterial enzymes DNA gyrase and topoisomerase IV.

SUMMARY OF INVENTION

A selection of N-acyl ciprofloxacin analogues, RC4-125, RC4-143, RC4-147, RC5-28, RC5-29, RC5-32 and RC5-69 (FIG. 1), which are chemically derived from ciprofloxacin and differ only in their side chains, are found to have significant antibacterial against Bartonella species.

The N-acyl ciprofloxacin analogues RC4-125, RC4-143, RC4-147, RC5-28, RC5-29, RC5-32 and RC5-69 can therefore be especially useful in the treatment of bacterial infections caused by Bartonella species.

BRIEF DESCRIPTION OF THE DRAWINGS

For a fuller understanding of the invention, reference should be made to the following detailed description, taken in connection with the accompanying drawings, in which:

FIGS. 5 and 6 shows two tables, Table 1 and Table 2. For select ciprofloxacin analogues, Kirby-Bauer disk diffusion zone sizes and minimum inhibitory concentrations (MICs) are indicated. Zones of inhibition were measured in mm MICs were determined by agar dilutions and measured in µg/mL. Values marked with * are obtained from Rolain J M, Broqui P, Koehler J E, Maguina C, Dolan M J, Raoult D: Recommendations for treatment of human infections caused by Bartonella species, Antimicrob Agents Chemother, 48(6): 1921-1933, 2004.

DETAILED DESCRIPTION OF THE PREFERRED EMBODIMENTS

In the following descriptions, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

A selection of N-acyl ciprofloxacin analogues, chemically synthesized from ciprofloxacin have been tested for in vitro activity against Bartonella species. Nine Bartonella strains, including five of B. henselae, two of B. quintana and one each of B. elizabethae and B. vinsonii, have been tested for susceptibility to ten N-acyl ciprofloxacin derivatives.

The Kirby-Bauer disk diffusion assay, agar dilution testing, DNA gyrase assay, broth dilution testing, and an HMEC-1 cell assay have been done in vitro to characterize the activity each fluoroquinolone compound, using ciprofloxacin as the control.

Seven of the fluoroquinalone compounds, viz. RC4-125, RC4-143 and RC4-147, RC5-28, RC5-29, RC5-32 and RC5-69 showed significant anti-Bartonella activity. These compounds gave zones of growth inhibition greater than 30 mm in disks impregnated with 20 µg of drug, minimal inhibitory concentrations of 0.1-10.0 µg/mL and significant activity against intracellular bacteria.

Figure 1:
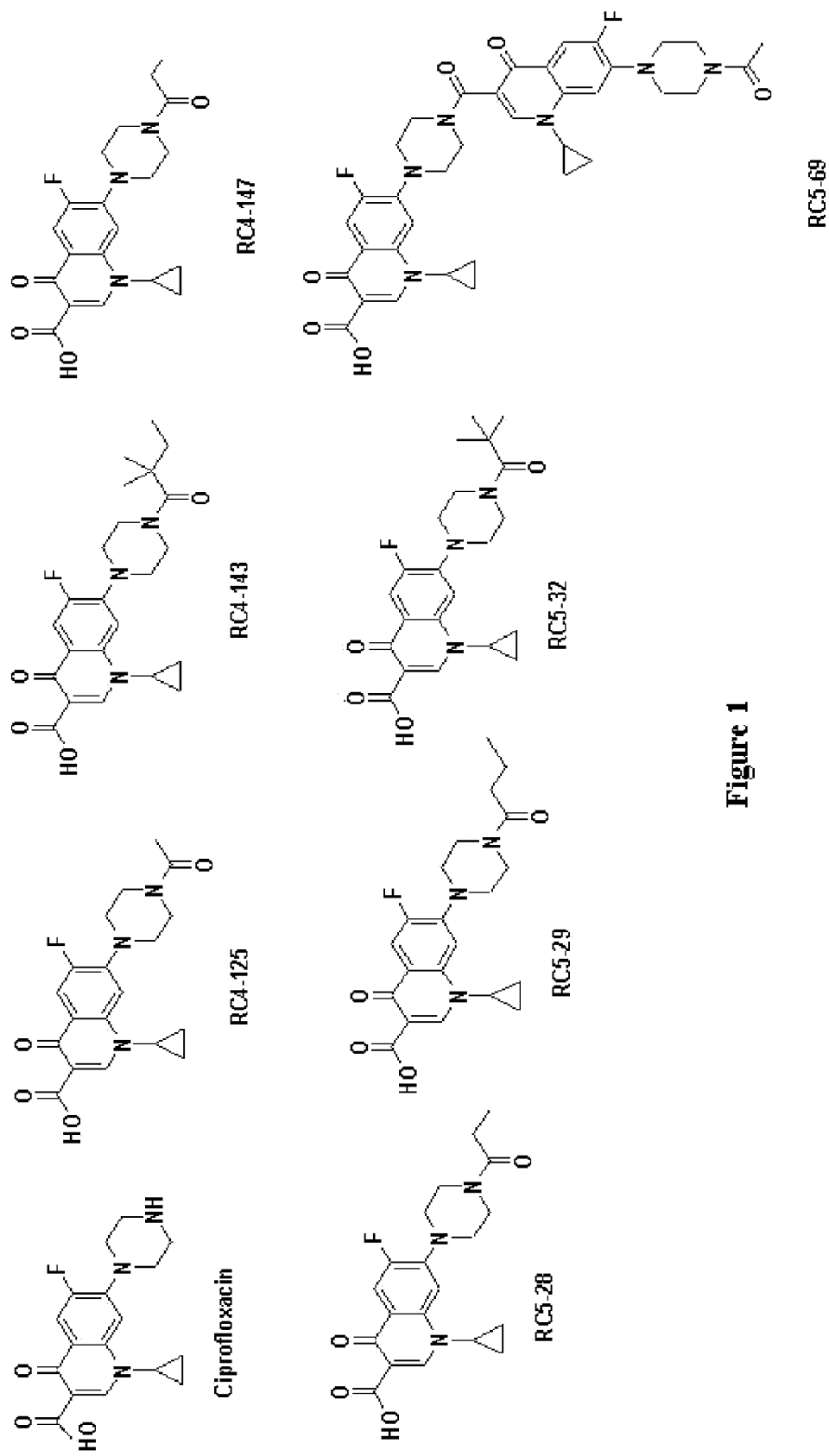
FIG. 1 is a schematic depiction of chemical structures of ciprofloxacin and three of the N-acyl ciprofloxacin analogues: RC4-125, RC4-143, RC4-147, RC5-28, RC5-29, RC5-32 and RC5-69.
Figure 2:
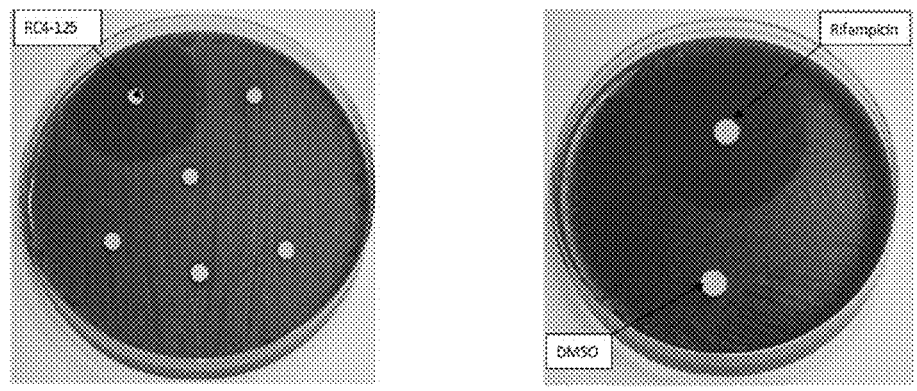
FIG. 2 is a schematic depiction of a Kirby-Bauer disk diffusion test of N-acyl ciprofloxacin analogues against Bartonella henselae Houston-1 rough. Each disk contained 20 µg of antibiotic, 2.0 µg of rifampicin as the control, or 20 µL of undiluted dimethylsulfoxide (DMSO). Zones of inhibition of bacterial proliferation are measured in mm.

Kirby-Bauer Disk Diffusion 6 mm paper disks were saturated with 20 µg of the fluoroquinalone compound to be tested or 2.0 µg of the rifampicin control in 20 µL of DMSO. The solvent control was 20 µL of undiluted DMSO. Nine strains of Bartonella were harvested from 4-day-old plates and resuspended in 1.0 mL sterile heart infusion broth (HIB) and adjusted to a McFarland 2.0 turbidity standard. Each suspension was spread onto a 150 mm chocolate agar plate and allowed to dry. Then, disks containing the fluoroquinalone compounds, rifampicin, or DMSO were placed on the plates in a designated pattern. Inoculated plates were incubated for 1 week, and the zones of inhibition were measured to the nearest mm. The results obtained are shown in FIGS. 2, 5 and 6.

Agar Dilution Testing

Agar was prepared with the N-acyl ciprofloxacin-derived compounds at concentrations of 10 µg/mL, 1.0 µg/mL and 0.1

μg/mL. An equivalent volume of DMSO was added to a control plate. Nine strains of *Bartonella* were harvested from 4-day-old plates, resuspended in 1.0 mL sterile HIB and adjusted to a McFarland 2.0 turbidity standard. Using a specific template, 12.5 μL of broth suspensions of each *Bartonella* strain was pipetted onto each of the fluoroquinalone compound-containing chocolate agar plates and the DMSO control plate. After 1 week, the growth of each *Bartonella* strain was examined and recorded.

Assay for Intracellular Activity

Figure 4:
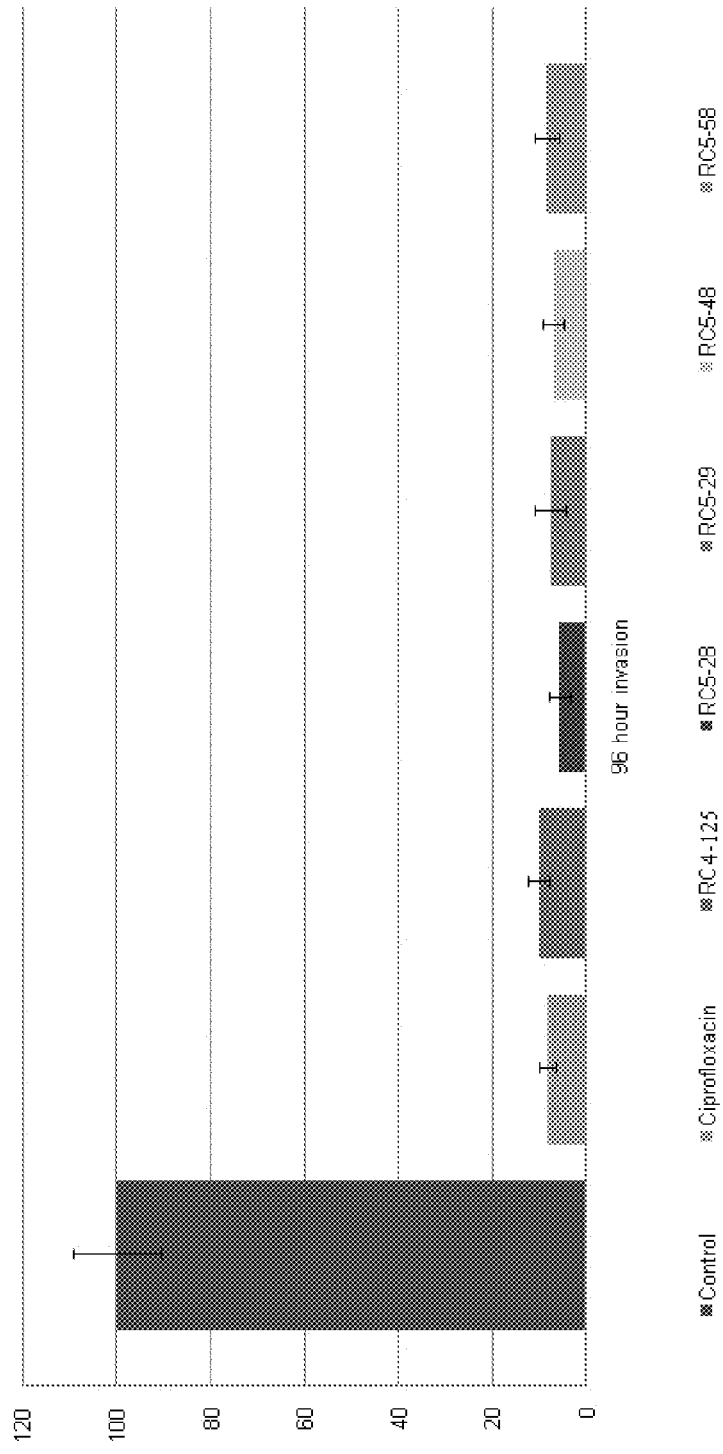
FIG. 4 is a schematic depiction of cell invasion results for 96 hour incubation time in 1.0 µg/mL of N-acyl ciprofloxacin derivatives. Values are shown as percentage of colony forming units in comparison to control which contained cell culture media only.

HMEC-1 cells were maintained in MCDB131 medium supplemented with 10% FBS, 5% L-glutamine, 10 ng/mL epidermal growth factor, 1 μg/mL hydrocortisone, penicillin/streptomycin and amphotericin B. HMEC-1 cells were infected with *Bartonella henselae* Houston-1 at a multiplicity of infection (MOI) of 100 for 4 hour in medium without ciprofloxacin-derived compounds. After infection, the cells were washed 2× with PBS and then treated with gentamicin (200 μg/mL) for 1 hour. Infected cells were washed as before and medium containing ciprofloxacin-derived compound was added at concentrations of 0.1 μg/mL, 1.0 μg/mL and 10 μg/mL. Infected cells were then incubated for 24, 48 and 96 hour. Ciprofloxacin-derived compounds were then removed, and the infected cells were washed as before and lysed with 0.1% saponin Lysates were plated on chocolate agar. After incubation for 8 days, CFU's were counted to determine the number of viable intracellular bacteria. Results are shown in FIG. 4.

Figure 3:
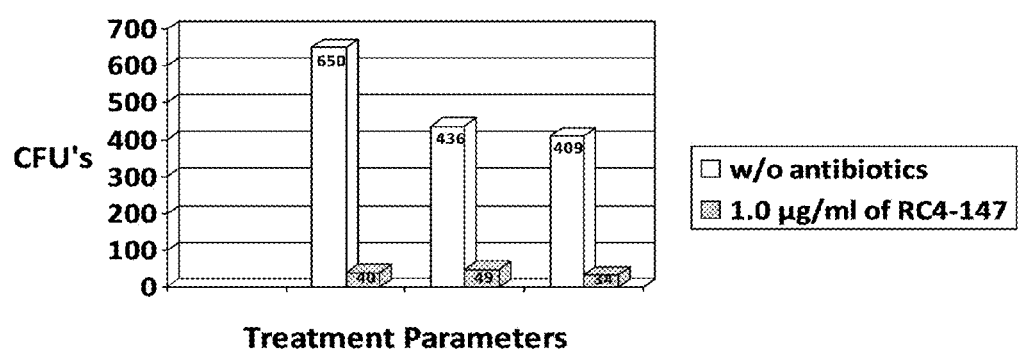
FIG. 3 is a schematic depiction of activity of N-acyl ciprofloxacin analogue RC4-147 against intracellular Bartonella henselae Houston-1. Results were obtained from 24-hour human mammary epithelial cell (HMEC) culture infections and are expressed as intracellular colony forming units (CFUs).

Compound RC4-147 showed greater than a tenfold decrease in CFUs when infected HMEC cells were treated with 1.0 μg/mL for 24 hours. This suggests that this synthetically-derived N-acyl ciprofloxacin derivative could be an effective therapeutic for the treatment of infections caused by intracellular bacteria such as *Bartonella*. Results are shown in FIG. 3.

Seven compounds, RC4-125, RC4-143, RC4-147, RC5-28, RC5-29, RC5-32 and RC5-69 showed unambiguous anti-Bartonella activity. These seven compounds gave zones of growth inhibition greater than 30 mm on disks impregnated with 20 lag of drug. MICs were 1.0-10.0 μg/mL for RC4-125, 0.1-0.5 μg/mL for RC4-143 and 0.1-0.2 μg/ml for RC4-147, RC5-28, RC5-29, 0.5-0.8 μg/mL for RC5-32 and RC5-69.

DNA Gyrase Analysis

Activity of each ciprofloxacin derivative against DNA gyrase was tested using relaxed circular pUC19 DNA in the presence of *E. coli* DNA gyrase at ciprofloxacin derivative concentrations of 1.0 μg/mL, 10 μg/mL and 25 μg/mL. Samples were incubated at 37° C. for 1 hour and then analyzed by gel electrophoresis to quantify the amounts of relaxed and supercoiled DNA. The DNA gyrase assay verified DNA gyrase as the target of the synthetically-derived N-acyl ciprofloxacin derivatives.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A compound represented by the formula:

or a pharmaceutically acceptable salt or ester thereof.

2. A method of treating *Bartonella* infection, comprising administering the compound of claim 1 to a subject in need thereof.

* * * * *